United States Patent
Dubois et al.

(10) Patent No.: US 9,120,996 B2
(45) Date of Patent: Sep. 1, 2015

(54) PROCESS OF REACTIVE TRITURATION DIRECTLY ON AN OIL CAKE

(75) Inventors: Jean-Luc Dubois, Millery (FR); Antoine Piccirilli, Poitiers (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/122,081

(22) PCT Filed: May 23, 2012

(86) PCT No.: PCT/FR2012/051159
§ 371 (c)(1),
(2), (4) Date: Nov. 25, 2013

(87) PCT Pub. No.: WO2012/160314
PCT Pub. Date: Nov. 29, 2012

(65) Prior Publication Data
US 2014/0096577 A1    Apr. 10, 2014

(30) Foreign Application Priority Data
May 25, 2011 (FR) ...................... 11 54554

(51) Int. Cl.
| | | |
|---|---|---|
| *C11C 1/02* | (2006.01) | |
| *C11B 1/04* | (2006.01) | |
| *C11C 3/00* | (2006.01) | |
| *C11B 13/00* | (2006.01) | |
| *C11B 1/06* | (2006.01) | |
| *C11B 1/10* | (2006.01) | |
| *C10L 1/02* | (2006.01) | |
| *C11C 1/08* | (2006.01) | |
| *C07C 67/03* | (2006.01) | |
| *C07C 67/48* | (2006.01) | |

(52) U.S. Cl.
CPC . *C11C 1/02* (2013.01); *C10L 1/026* (2013.01); *C11B 1/04* (2013.01); *C11B 1/06* (2013.01); *C11B 1/10* (2013.01); *C11B 13/00* (2013.01); *C11C 1/08* (2013.01); *C11C 3/003* (2013.01); *C07C 67/03* (2013.01); *C07C 67/48* (2013.01); *Y02E 50/10* (2013.01); *Y02E 50/13* (2013.01); *Y02E 50/30* (2013.01); *Y02E 50/343* (2013.01); *Y02W 30/47* (2015.05); *Y02W 30/74* (2015.05)

(58) Field of Classification Search
None
See application file for complete search history.

(56) References Cited

U.S. PATENT DOCUMENTS

| | | |
|---|---|---|
| 2006/0069274 A1 | 3/2006 | Dias De Moraes E Silva et al. |
| 2007/0099278 A1 | 5/2007 | Aare |
| 2007/0260079 A1 | 11/2007 | Fleisher |
| 2009/0038209 A1 | 2/2009 | Farid et al. |
| 2010/0008886 A1* | 1/2010 | Tosaki et al. ................. 424/74 |
| 2010/0307051 A1* | 12/2010 | Tremblay et al. .............. 44/388 |

FOREIGN PATENT DOCUMENTS

| | | | | |
|---|---|---|---|---|
| EP | 2243379 | * | 10/2010 | ............ A23D 9/00 |
| JP | 2004091782 A | * | 3/2004 | ............ C11B 13/00 |
| WO | WO 2007/049979 A1 | | 5/2007 | |
| WO | WO 2007/130346 A1 | | 11/2007 | |
| WO | WO 2010076527 A1 | * | 7/2010 | ............ C11C 3/00 |
| WO | WO 2010120939 | * | 10/2010 | ............ C11B 1/04 |

OTHER PUBLICATIONS

JP 2004091782A, Nishida et al, 2004, Method for recycling oil cake . . . , English translation, 20 pages.*
Shuit, S.H., et al., Reactive extraction and in situ esterification of *Jatropha curcas* L. seeds for the produciton of biodiesel, 2010, Fuel, vol. 89, pp. 527-530.*
International Search Report (PCT/ISA/210) mailed on Aug. 8, 2012, by the European Patent Office as the International Searching Authority for International Application No. PCT/FR2012/051159.

* cited by examiner

*Primary Examiner* — Yate K Cutliff
(74) *Attorney, Agent, or Firm* — Buchanan Ingersoll & Rooney P.C.

(57) ABSTRACT

A process including at least one reactive trituration step which includes putting an oil cake including from 3% to 30% oil in contact with an anhydrous light alcohol and an alkaline catalyst under temperature and time conditions that are sufficient to allow for the extraction and transesterification of the vegetable oil and lead to the production of a mixture including fatty acid esters and glycerol, and a de-oiled cake including less than 3% oil. Also, a detoxified de-oiled cake as well as to a mixture of fatty acid esters with improved stability and resistance to oxidation.

17 Claims, No Drawings

PROCESS OF REACTIVE TRITURATION DIRECTLY ON AN OIL CAKE

The present invention relates to a process for the reactive trituration of an oil cake, to extract fatty acid esters therefrom.

An "oil cake" is a solid residue generally obtained from a process of pressing oil-yielding plant seeds to recover oil (known as first cold-pressing or hot-pressing oil). The cake may also be derived from a "double-pressing" process, comprising a first pressing of the oil-yielding seeds followed by a second step of pressing of the cake produced during the preceding step. The oil cake may contain from 3% to 30% oil.

The oil recovered from the seeds of oil-yielding plants is for food, energy or industrial use. The pressing of the seeds of oil-yielding plants, such as rapeseed and sunflower, developed especially to provide oil for use as a fuel.

This oil production is accompanied by a large production of oil cakes, which it is necessary to upgrade as best as possible, in order to optimize the overall economic balance for this transformation.

Certain oil cakes, of rapeseed and of soybean, for example, may be of interest in livestock rearing for animal nutrition. However, "de-oiled" cakes are generally used, containing less than 3% oil. Their nutritional value is more advantageous, their protein content is higher and their fat content is lower than for oil cakes. Furthermore, oil cakes have a tendency to turn rancid, which reduces the animal's appetite for this type of food.

It is known practice to extract the remaining oil of oil cakes by counter-current percolation of a solvent (such as hexane) heated to 40-60° C. for 4 to 5 hours. The mixture of oil and solvent then needs to be distilled in order to separate them by heating to 115-120° C. under suction and injection of steam. The cakes thus "de-oiled" contain 0.5% to 2.5% oil. However, the steps of this solvent-mediated oil extraction process are energy-intensive. Moreover, given the highly volatile and flammable nature of hexane, these steps are classified as hazardous and lead to a substantial release of volatile organic compounds into the environment. The oil extracted from the cake is of mediocre quality compared with the oil of first cold-pressing, and must be refined. This is because the hexane-extracted oils are rich in undesirable compounds, such as phospholipids. Furthermore, the acidity of the extracted oil is high, close to that of the starting oil cakes, which themselves have a tendency to concentrate free fatty acids. This acidity of the oil has the drawbacks of leading to the production of soaps during the transesterification operations for the production of biodiesel, but also of reducing the cold stability of the oil. The presence of free fatty acids also complicates the refining process.

The oils thus extracted and refined are in some cases edible, and in others only used in paint, in soap manufacture (by saponification of the oil), in pharmacy and cosmetics, in industry and in oil chemistry for the production of fatty acids, etc.

By transesterification of the oil in the presence of alcohol and a catalyst, fatty acid esters used in biofuels are in particular manufactured. According to the known techniques of the prior art, the manufacture of these esters from oil cakes would thus require at least two main steps: extraction of oil from the cake and then transesterification, these same steps being broken down into several sub-steps.

The aim of the present invention is thus to provide a novel, simpler process, which has the fewest possible steps, for upgrading oil cakes.

The Applicant has now found such a process for manufacturing in a single step fatty acid esters from oil cakes.

One subject of the present invention is thus a process comprising at least a step v) of reactive trituration which consists in placing an oil cake comprising from 3% to 30% oil in contact with an anhydrous light alcohol and an alkaline catalyst under temperature and time conditions that are sufficient to allow the extraction and transesterification of the plant oil and that lead to the production of a mixture comprising fatty acid esters and glycerol, and a de-oiled cake comprising less than 3% oil.

The term "light alcohol" means a lower aliphatic alcohol in which the number of carbons is within the range from 1 to 8, preferably from 1 to 5 or better still from 1 to 4. The light alcohol is advantageously chosen from methanol, ethanol, isopropanol, n-propanol, butanol, isobutanol and 2-ethylhexanol, and mixtures thereof. According to one preferred embodiment of the invention, the light alcohol is methanol.

The alkaline catalyst used in the process is chosen from the group: sodium hydroxide, alcoholic sodium hydroxide, solid sodium hydroxide, potassium hydroxide, alcoholic potassium hydroxide, solid potassium hydroxide, sodium or potassium methoxide, sodium or potassium ethoxide, sodium and potassium propoxide, and sodium and potassium isopropoxide. According to one preferred embodiment of the invention, the alkaline catalyst is sodium hydroxide.

The oil cake used in the process of the invention is obtained from seeds of any type of oil-yielding plant: almond, groundnut, safflower, hemp, rapeseed, coconut, cotton, shea, flax, corn, mustard, rape, walnut, olive, cabbage palm, poppy, castor-oil plant, jatropha, lesquerella, sea kale, camelina, sesame, soybean and sunflower are examples thereof.

It would not constitute a departure from the context of the invention if the cakes used in the process according to the invention were to originate totally or partly from genetically modified oil-yielding plants.

Preferably, the oil cake has an acidity content that is in the range from 1 to 10 mg KOH/g, preferably from 1 to 8 mg KOH/g and preferably from 1 to 6 mg KOH/g, in order to avoid saponification reactions that reduce the ester yield. This acidity of the oil cake is largely associated with the conditioning to which the cake has been subjected after its production.

The oil cake is used alone or as a mixture with whole seeds (with their husk), these seeds originating from the same plant or from another oil-yielding, oil-protein-yielding or protein-yielding plant, said seeds preferably having an acidity content of less than 3 mg KOH/g. These mixtures preferably comprise at least 50% by weight of oil cake relative to the total weight of the mixture. These mixtures have several advantages. First, they make it possible to reduce the overall acidity content of the triturated material, since the cakes have a tendency to be more acidic than the seeds from which they are derived. Now, low acidity levels make it possible to improve the ester yield of the process. Second, the addition of seeds with their husk makes it possible to curb the lubricant effect of the oil cakes and improves the cohesion of the charge to be treated, by creating by compression a sort of "stopper" that increases the percolation and thus also improves the yield for the trituration reaction. The compressed mixtures of cake and seeds may especially easily withstand several percolation cycles during the trituration step v). These cake-seed mixtures make it possible to increase the area of contact for better percolation of the alcohol-catalyst mixture and thus better extraction of the lipids and their consecutive transformation into esters.

For the purposes of the invention, the term "oil cake" means a cake that contains 3% to 30% fat, or even rather 5% to 25% and preferably 7% to 20% fat. In contrast with the "de-oiled cake" containing less than 3% fat, the oil cake used in the present invention has not undergone extraction or washing with any solvent.

In the present description of the invention, the terms "oil" and "fat" are used independently to denote the lipids that are or are not extracted from the cake.

The oil content of the oil cakes used in the present invention varies as a function of the pressing conditions and of the seeds used. "Agricultural" oil cakes and "industrial" oil cakes are generally distinguished. Pressing at a farm is performed without a cooking pretreatment of the seeds, and the oil cakes have a fat content that ranges from 12% to 30%. In the case of semiindustrial or industrial installations, the pressing produces less fatty cakes, generally according to one of the following two processes. In cold batch or continuous pressing, the products are ground, crushed or flattened. The oil (especially olive oil and walnut oil) is extracted by successive presses at a temperature below 80° C. The yield is low, the cakes conserving 6% to 12% fat. In continuous hot pressing, the seeds are preheated up to 90° C., ground or flattened and then pressed in an endless screw in which the temperature will be up to 120° C. Another industrial variant consists in performing a second pressing step on the cake obtained from the first seed pressing. The yield is improved. 4% to 20% oil remains in the cake, depending on the seeds and the installations.

Advantageously, the reaction takes place in a fixed-bed reactor. According to one embodiment, the fixed-bed reactor is a temperature-regulated percolation column equipped with a grille. A pump feeds the column with alcohol-basic catalyst mixture. The alcohol and the catalyst are thus added simultaneously to the reactor, which is maintained at a temperature ranging from 30 to 75° C., preferably less than or equal to 70° C., preferably less than 45° C., and preferably at about 40° C. The catalyst/alcohol/cake mass ratio is preferably within the range 0.001 to 0.01/0.1 to 10/1 and preferably from 0.001 to 0.01/0.1 to 5/1, preferably in the range from 0.002 to 0.01/0.1 to 3/1 and even more preferably in the range from 0.002 to 0.01/0.1 to 2/1.

In particular, a catalyst content of less than 0.001 or even less than 0.002 does not make it possible to obtain a sufficient yield of ester (i.e. a yield of at least 50%) or a sufficient conversion of the triglycerides, diglycerides and especially of the monoglycerides. Conversely, a content of greater than 0.01 leads to saponification and thus also to a poor yield of esters.

The introduction is performed at the top of the bed; the reaction liquid then percolates through the bed and is recovered in a reserve located downstream, under the bed. By pumping, the liquid is sent back to the top of the bed to diffuse again in the bed. The duration of the recirculation cycle of the alcohol/catalyst mixture is from 15 to 60 minutes and preferably from 20 to 40 minutes. At the end of the cycle, the liquid feed is stopped. Part of the liquid that is still present in the soaked cake is then recovered by simple draining over a period of 10 to 20 minutes. The recovered liquid may undergo a step of neutralization by addition of acid, and then a step of evaporation of the alcohol, to give a mixture of phases containing a lighter phase that is rich in esters and a denser phase that is rich in glycerol. The phase mixture is subjected to a decantation step (which consists, for example, of static decantation in one or more decanters in parallel or in series, centrifugal decantation, or a combination of static or centrifugal decantation), making it possible to obtain an upper phase predominantly composed of fatty acid esters (ester phase) and a lower phase predominantly composed of glycerol and water (glycerol phase).

The ester phase is then subjected to a sequence of chemical reactions and/or of separations/purifications directed towards recovering the fatty esters, comprising, in a known manner, a step of washing with water followed by a step of drying under vacuum.

The fatty acid ester thus obtained is intended especially for the preparation of biodiesel.

The other product obtained directly from the process according to the invention is the de-oiled cake. The de-oiled cake according to the invention contains less than 3% oil, preferably less than 2%, or better still less than 1% by weight of oil, relative to the weight of the cake.

The process according to the invention may without difficulty be performed continuously at the industrial scale, for example using: a moving-band reactor-extractor operating continuously (such as a De Smet extractor); a rotary filter, a centrifuge or a centrifugal decanter. Preferably, the reactive trituration is performed with methanol passing counter-currentwise through the cake, over several consecutive stages.

According to one embodiment variant, an organic solvent (cosolvent) that is miscible or immiscible with the said light alcohol is also added to the reaction medium. In this case, the trituration step v) comprises the simultaneous introduction into a reactor containing the said cake, of the anhydrous light alcohol, of the basic catalyst and also of cosolvent. The latter is selected from the following group: hexane, heptane, benzene, bicyclohexyl, cyclohexane, decalin, decane, light spirit, petroleum ether, kerosene, kerdane, diesel oil, lamp oil, methylcyclohexane, naphtha (Texsolve V), skellite, tetradecane, Texsolve (B, C, H, S, S-2, S-66, S-LO, V), supercritical $CO_2$, pressurized propane or butane, natural solvents such as terpenes (limonene, alpha and beta pinene), ethers such as dimethyl ether, diethyl ether, ketones such as acetone, and mixtures of all these solvents.

Preferably, the light alcohol/cosolvent ratio is within the range from 10/90 to 90/10.

Advantageously, the process according to the invention also comprises, before the trituration step v), at least one step ii) of pressing of oil-yielding plant seeds to recover part of the oil of the seeds and to manufacture the said oil cake. Any device and process known for this pressing step may be envisaged, such as those already described above.

Optionally, the pressing step ii) is preceded by at least one of the following steps i): crushing, hulling, preheating and/or drying of the seeds.

The term "crushing" of the seeds means a coarse reduction of the size of the seed, which, as a function of its initial size, may be divided into two or more parts that are more or less fine. This operation may be performed, for example, on a corrugated-roll flattener or on a pin mill or a knife mill.

The term "hulling" of the seeds means the separation of the constituents of the seed that are the kernel and the silverskin surrounding it. This operation contributes towards ridding the seed of a non-oily constituent, the silverskin, thus simultaneously making it possible to increase the oil productivity of the process and also the protein content of the cake.

The term "preheating" of the seeds means a hot thermal treatment at a temperature within the range from 50 to 90° C. and preferably from 70 to 80° C. of the seed, making it possible, depending on the desired objective:

to increase the fluidity of the oil,
   to increase the plasticity of the seed to be pressed,
   to coagulate the proteins.

The term "drying" of the seeds means heating of the seed at a temperature in the range from 60 to 140° C. in order, depending on the desired objective:

to adjust the moisture content of the seed to between 0.5% and 5%, to destroy certain microorganisms (e.g. salmonella), to deactivate the heat-sensitive enzymes (e.g. lipases), to decompose the thermolabile toxic substances.

According to a preferred embodiment of the invention, to facilitate the percolation of the solvent (based on anhydrous light alcohol and on alkaline catalyst) through the three-dimensional lattice of the cake, the cake is "flaked" before the reactive trituration step v). This flaking step iii) consists in crushing the cake in order to destructure its three-dimensional network without evacuating fat from the cake.

Advantageously, the oil cake is dried (drying step iv)) before the reactive trituration step v), preferably just after its manufacture, after step ii), for example in a continuous hot-air dryer, at a temperature of between 60 and 140° C. in order to achieve a relative moisture content of less than or equal to 2%. Preferably, less than 72 hours, preferably less than 48 hours, preferably less than 24 hours and preferably less than 12 hours pass between step ii) of manufacture of the oil cake and the reactive trituration step v). Advantageously, the steps of the process according to the invention are performed continuously. These preferred embodiments have the aim of performing the trituration step v) on a "freshly prepared" oil cake, preventing it from becoming oxidized, hydrated and hydrolyzed forming free fatty acids.

According to one advantageous embodiment of the process of the invention, the cake is first flaked by simple flattening or multiple flattening, and then dried before being used in reactive trituration performed in the presence or absence of a cosolvent.

The process according to the invention makes it possible to react "in planta" the light alcohol with the oil contained in the core of the cake. In this process, the alcohol acts both as solvent and as reagent. The process according to the invention makes it possible to pass directly from the cake to the fatty acid esters, without prior extraction of the oil, avoiding the steps of refining, purification and production of by-products such as bleaching earths normally obtained during a filtration step, gums composed predominantly of phospholipids, and/or soaps derived from refining (neutralization of the free fatty acids).

The process of reactive trituration of the oil cakes according to the invention leads to the simultaneous production of a de-oiled cake, glycerol and fatty acid esters. For example, jatropha esters are obtained in the case of a jatropha oil cake, or castor oil esters including ricinoleic acid ester in the case of a castor-oil oil cake. The ricinoleic acid ester is intended mainly for the manufacture of 11-aminoundecanoic acid, the constituent monomer of Rilsan® 11, which is a polyamide with exceptional physical properties, developed by the Applicant. These esters are also suitable for the manufacture of biofuels.

The subject of the invention is especially a mixture of fatty acid esters, especially of fatty acid methyl esters, which may be obtained via the process of the invention, and which have a tocopherol content of greater than 10 mg/100 g. These natural antioxidants present in plant oils impart better stability and better resistance to oxidation of the mixture according to the invention. Furthermore, in contrast with esters derived from a conventional extraction with hexane, which must be refined in order to avoid the production of soaps, the fatty acid esters according to the invention may be used directly, for example as biofuel, without a prior refining step.

According to one embodiment variant, the alcohol-soaked de-oiled cake is dried in a ventilated oven for 4 hours at a temperature of less than or equal to 200° C., preferably less than or equal to 150° C. and even more preferentially less than or equal to 120° C. This drying step makes it possible to remove from the cake the solvent (alcohol) used during the extraction. This drying step also makes it possible to destroy any toxins and allergens that may be remaining in the cake.

According to another embodiment variant, the process according to the invention does not comprise a step of drying the cake at high temperature (temperature above 120° C.); according to the conditions used, any toxins and allergens may be inactivated by means of the physical and/or chemical treatments applied to the oil cakes during the steps of the process of the invention described above, such that the operation of drying of the cake at high temperatures becomes unnecessary. In this case, the process comprises only one step of drying of the cake at temperatures below 120° C., which is intended to remove the solvent (alcohol) used during the extraction, in order to allow the use of the said cake in animal feed.

Advantageously, the process according to the invention makes it possible to obtain completely de-oiled cakes, which keep their physical integrity (cohesion, mechanical strength) and which are detoxified and de-allergenized, in which any toxins and allergens have been inactivated.

Phorbol esters, for example, are the main source of toxicity of Jatropha cakes. This family of compounds is known for its harmful biological effects in man and animals, especially in inflammation and the promotion of tumours. Advantageously, the detoxified de-oiled cake(s) according to the invention have a content of phorbol esters of less than or equal to 0.3 mg/g and preferably less than 0.2 mg/g.

Among the inactivated toxins, examples that may also be mentioned include ricin present in castor-oil oil cakes, or curcin present in jatropha oil cakes. Among the allergens, mention may be made of the allergen CB-1A present in castor-oil oil cakes. Assays of toxins, such as ricin, in the cake before and after de-oiling show that the best cake detoxification results are obtained in the case of the process according to the invention, by virtue of the simultaneous presence of light alcohol and of alkaline catalyst. In contrast, the standard extraction processes (unreactive trituration) on the cakes with solvent, for example with hexane and/or methanol, always leave high contents of toxins in the cake. The best detoxification results are obtained by reactive trituration according to the invention using methanol and sodium hydroxide. It is noted in particular that the light alcohol used alone (without cosolvent) in the presence of alkaline catalyst gives better detoxification results than mixtures of light alcohol with cosolvent (for example hexane) still in the presence of alkaline catalyst, which themselves give better cake detoxification results than the standard extraction processes without alkaline catalyst. It is thought that it is the alkaline catalyst used in the present process that entails the noteworthy cake detoxification effect. This effect is all the more observed when the starting cake used in the process of the invention is less acidic. Specifically, in the case of acidic oil cakes (acid number of greater than or equal to 10 mg KOH/g), the alkaline catalyst rather has a tendency to neutralize the free fatty acids of the cake to form soaps and cannot fully participate in the detoxification of the cake.

The detoxified cakes according to the invention are of nutritional value and may be used directly in animal feed, without constituting a risk to the health of the persons handling them.

Besides food applications, the de-oiled cakes according to the invention are rich in nitrogen and may also be used as fertilizer or as fuel. They may be used as charcoal (after carbonization of the cake), optionally activated to make active charcoal, as vegetable filler in biosourced composite materials, as biocarbon used in agriculture, or alternatively for the manufacture of biogas, as a source of nitrogen for microorganisms in methanization reactions to produce energy in the form of methane.

The invention and its advantages will be understood more fully on reading the examples below, which are given for purely illustrative and non-limiting purposes.

EXAMPLES

Unless otherwise indicated, all the percentages are given on a weight basis. In the examples below, the reactive trituration process according to the invention is performed on cakes derived from an extraction step by mechanical pressing.

Example 1

Reactive Trituration Test on a Jatropha Pressing Cake

Preparation of the Jatropha Cake

Before pressing the jatropha seeds on a Taby 40A press, the jatropha seeds are precrushed on a pin-roll flattener.

TABLE 1

Parameters of the mechanical pressing of the jatropha seeds

| Materials | Parameters | Comments |
|---|---|---|
| Tool | single screw | Taby press |
| Die diameter, mm | 12 | semi-conical die |
| Preheating of the seed | yes | Temperature of 70 to 80° C. |

TABLE 2

Material balance for the mechanical pressing of the jatropha seeds

| Material entering | |
|---|---|
| Double-flattened jatropha seeds g | 6848 |
| Volatile matter content, % RM** | 7.5 |
| Fat content, % DM* | 35.0 |
| Material exiting | |
| Oil cake, g | 4863 |
| Volatile matter content, % RM** | 9.0 |
| Fat content, % DM | 13.6 |
| Unfiltered raw pressing oil, kg | 1985.1 |

*DM = dry matter
**RM = raw material

The cake prepared has a fat content of 13.6%. This cake is immediately dried at 100° C. for 16 hours.

Example 2

Reactive Trituration Test on a Jatropha Pressing Cake

The reactive trituration is performed in a percolation column equipped with a fixed bed. It is performed under the following conditions:
1. The raw cake as exiting the press, of cylindrical form (length=20 mm, diameter=12 mm), is dried in an oven at 100° C. for 16 hours. Its relative moisture content is 0.8%.
2. The dried cake is introduced into the percolation column (350 g).
3. Methanolic sodium hydroxide solution at 0.4% relative to the cake is then recirculated through the bed for 30 minutes at 50° C.
4. The miscella is then drawn off and the flake bed is then washed by 5 successive washes with methanol at 50° C. (5 minutes per wash).

In view of the results of Table 3, it turns out that, under the test conditions, the ester yield is 50%. This low yield is linked to a high saponifying activity (high yield of glycerol, greater than 100% by weight since it contains other compounds).

TABLE 3

Optimization of the catalyst content on the jatropha cake

| TEST | 10-E36 |
|---|---|
| Catalyst content (vs oil cake), % | 0.4 |
| Reaction and extraction temperature | 50 |
| Methanol/oil cake mass ratio | 1.6 |
| Yield of solids (1), % | 94.5 |
| Ester/glycerol phase separation | yes |
| Ester yield, % | 50.2 |
| Glycerol yield, % | 533 |
| Cake ester potential, % | 17.6 |
| Fat content of the de-oiled cake, % DM* | 2.6 |
| Loss of ester (2), % | 32.2 |

(1) The yield of solids is the ratio times 100 of the solids obtained after evaporation of the miscella to the sum of the theoretical amounts of ester and glycerol
(2) Loss of ester = 100 − ester yield − cake ester potential
*DM = dry matter In qualitative terms (Table 4), the ester produced with 0.4% of catalyst engaged, has moderate acidity and a moderate glyceride content.

TABLE 4

Analytical balance of the jatropha esters

| Criterion | 10-E36 |
|---|---|
| Acid number (mg KOH/g) | 0.5 |
| Monoglyceride content (%) | 0.8 |
| Diglyceride + triglyceride content (%) | 0.15 |

In the presence of pressing cake, which is in the form of cylindrical pellets, it is observed that the percolation rate of the methanolic sodium hydroxide solution supplied in a [methanol/cake] ratio of 1.6 is very high.

This is why, in the following tests, it is sought to improve the lipids-methanolic sodium hydroxide contact time and also the extractability of the fat by reducing the [methanol/cake] ratio, but also by performing the test in the presence of cosolvent (hexane in this case).

Example 3

Adaptation of the Amounts of Cosolvent and of Catalyst

The reactive trituration is performed in a percolation column equipped with a fixed bed. It is performed under the following conditions:
1) The crude cake as exiting the press, of cylindrical shape (length=20 mm, diameter=12 mm), is dried in an oven at 100° C. for 16 hours. Its relative moisture content is 0.8%.
2) The dried cake is introduced into the percolation column (350 g).

3) The solution consisting of methanolic sodium hydroxide at 0.27% (relative to the cake) and of hexane is then recirculated through the bed for 30 minutes at 40° C.
4) The miscella is then drawn off and the flake bed is then washed by 5 successive washes with a mixture of methanol and hexane (in a 90/10 mass ratio at 40° C. (5 minutes per wash)).

In test 10-E43 (Table 5 below), the reactive trituration temperature was reduced by 10° C. (50→40° C.) in order to avoid evaporation of the hexane. Under the test conditions (conditions adapted to the fat content of the cake) and by comparison with the test without cosolvent, it appears that the ester yield for the process according to the invention is improved (50→58%), especially by virtue of the presence of cosolvent.

TABLE 5

Material balance for the test performed in the presence of cosolvent

| TEST | 10-E43 |
|---|---|
| Fat content, % DM* | 13.6 |
| Catalyst content (vs oil cake), % | 0.27 |
| MeOH/hexane quality | 90/10 |
| MeOH/hexane/oil cake ratio | 0.72/0.08/1 |
| Yield of solids (1), % | 85.0 |
| Ester/glycerol phase separation | yes |
| Ester yield, % | 58.0 |
| Glycerol yield, % | 356 |
| Cake ester potential, % | 18.3 |
| Fat content of the de-oiled cake, % DM* | 2.8 |
| Loss of ester (2), % | 23.7 |

(1) The yield of solids is the ratio times 100 of the solids obtained after evaporation of the miscella to the sum of the theoretical amounts of ester and glycerol
(2) Loss of ester = 100 − ester yield − cake ester potential
(3) DM* = dry matter

TABLE 6

Analytical balance for the jatropha esters

| Criterion | Method | 10-E43 |
|---|---|---|
| Acid number (mg KOH/g) | EN14104 | nd |
| Monoglyceride content (%) | Arkema | 2.4 |
| Diglyceride and triglyceride content (%) | Arkema | 3.9 |

Example 4

Adaptation of the Amounts of Cosolvent and of Catalyst

In the following test, the amounts of hexane and of catalyst were increased to increase the transesterifying activity.

The reactive trituration is performed in a percolation column equipped with a fixed bed. It is performed under the following conditions:
1) The cake undergoes a preliminary operation of simple flattening on a flattener equipped with smooth rolls (spacing of 0.05 mm) followed by drying in an oven at 100° C. for 16 hours. Its relative humidity content is 1.5%.
2) The dried cake is then introduced into the percolation column (350 g).
3) The solution consisting of methanolic sodium hydroxide at 0.7% (relative to the cake) and of hexane (50/50 mass mixture) is then recirculated through the bed for 30 minutes at 40° C.
4) The miscella is then drawn off and the flake bed is then washed by 5 successive washes with a mixture of methanol and hexane (in a 50/50 mass ratio at 40° C. (5 minutes per wash)).

Under the conditions of test 10-E51 (see Table 7 below), the reactive trituration temperature is still 40° C. Under these conditions, it is observed that the increase in hexane content and in catalyst content has a positive effect on the yield of esters (>80%) and also on the depletion of the cake (0.2% residual fat).

TABLE 7

Material balance for the reactive trituration test on flaked cake performed at higher contents of hexane and of catalyst

| TEST | 10-E51 |
|---|---|
| Fat content of cake No. 2, % DM* | 18.7 |
| Oil acidity of the cake, mg KOH/g | 6.0 |
| Catalyst content (vs oil cake), % | 0.7 |
| Methanol/hexane/oil cake (flaked) ratio | 1/1/1 |
| Yield of solids (1), % | 110.4 |
| Ester/glycerol phase separation | yes |
| Ester yield, % | 80.5 |
| Glycerol yield, % | 407.7 |
| Cake ester potential, % | 0.7 |
| Fat content of the de-oiled cake, % DM* | 0.2 |
| Loss of ester (2), % | 18.8 |

(1) The yield of solids is the ratio times 100 of the solids obtained after evaporation of the miscella to the sum of the theoretical amounts of ester and glycerol
(2) Loss of ester = 100 − ester yield − cake ester potential
(3) DM* = dry matter Despite the acidity of the starting cake fat, which is initially high: 6 mg KOH/g, the esters produced according to the process of the invention have moderate acidity with an acid number of less than 0.5 mg KOH/g (Table 8).

TABLE 8

Analytical balance for the jatropha esters

| Criterion | Method | 10-E51 |
|---|---|---|
| Acid number (mg KOH/g) | EN14104 | 0.46 |
| Monoglyceride content (%) | Arkema | 1.1 |
| Diglyceride and triglyceride content (%) | Arkema | 0.2 |

Example 5

Detoxification of the Jatropha Cakes

Analytical Technique:
To evaluate the detoxification of the cakes in the present description of the invention, including in the examples, the preparation of the samples and the assay of the phorbol esters were performed according to the method of Makkar (Makkar H P S, Becker K, Sporer F, Wink M (1997) Studies on nutritive potential and toxic constituents of different provenances of *Jatropha curcas*. J. Agric. Food Chem. 45:3152-3157).

Preparation of the Samples:
The liquid samples are diluted in methanol and then injected. For the solid samples, the phorbol esters are first extracted with a mortar and pestle with methanol, and the alcoholic extracts are then injected.

Operating Conditions:
Detector: diode array (integration of the peaks at 280 nm).
Column: C18 reverse phase (LiChrospher 100, 5 μm), 250×4 mm+precolumn.
Oven: 22° C. (room temperature)

Eluents: B=acidified water (1.75 ml H$_3$PO$_4$ (85%) in 1 L of H$_2$O)
A=acetonitrile

TABLE 9

| Gradients | | |
|---|---|---|
| | Acidified water B (%) | Acetonitrile A (%) |
| 0 to 1 min | 60 | 40 |
| 1 to 10 min | 50 | 50 |
| 10 to 40 min | 25 | 75 |
| 40 to 55 min | 0 | 100 |
| 55 to 70 min | 0 | 100 |

Flow rate: 1.3 ml/min.
Assay of the Phorbol Esters in the First Pressing Cake Produced in Example 1:

TABLE 10

| Assay of the phorbol esters of the jatropha cake | | |
|---|---|---|
| | Content of phorbol esters mg/g | Distribution of the phorbol esters (as % of PE of the seed) |
| Seed engaged (3) | 3.5 | 100 |
| Oil cake | 2.4 | 50.1 |

The first-pressing cake still remains with a very high concentration of phorbol esters (PE), i.e. the equivalent of 50% of the PEs of the starting seed.
Assay of the Phorbol Esters in the Cake Derived from the Reactive Triturion Process and Produced in Example 4:

TABLE 11

| Distribution of the phorbol esters in the reactive trituration test-Test 10E51 (reactive trituration test with 50/50 methanol/hexane cosolvent) | | |
|---|---|---|
| | Content of PE mg/g | Distribution of the PEs (as % of PEs of the seed) |
| Cake (1) | 0.1 | 1.7 |

(1) Drying temperature = 100° C., 16 hours.

The cake obtained from the process according to the invention of reactive trituration on a pressing cake with cosolvent is much more detoxified than that obtained from a first-pressing process. Its content of phorbol esters (PE), i.e. 0.1 mg/g of cake, in effect corresponds to 1.7% of the PEs of the seed. The reactive trituration process performed on a first-pressing cake is indeed a detoxifying process.

The invention claimed is:

1. Process comprising at least one reactive trituration step v), the trituration step v) consisting of: placing an oil cake comprising from 3% to 30% oil in contact with an anhydrous light alcohol, an alkaline catalyst, and, optionally, a cosolvent, under temperature and time conditions that are sufficient to allow the extraction and transesterification of plant oil and leading to the production of a mixture comprising fatty acid esters and glycerol, and a de-oiled cake comprising less than 3% oil.

2. Process according to claim 1, in which the trituration step v) consists of the simultaneous introduction, into a reactor containing the oil cake, of anhydrous light alcohol, of alkaline catalyst and also of a cosolvent selected from the group: hexane, heptane, benzene, bicyclohexyl, cyclohexane, decalin, decane, light spirit, petroleum ether, kerosene, kerdane, diesel oil, lamp oil, methylcyclohexane, naphtha (Texsolve V), skellite, tetradecane, Texsolve (B, C, H, S, S-2, S-66, S-LO, V), supercritical CO$_2$, pressurized propane or butane, terpenes (limonene, alpha and beta pinene), ethers, ketones, and mixtures of all these solvents.

3. Process according to claim 1, also comprising, before the trituration step v), at least one step ii) of pressing of seeds of oil-yielding plants to recover part of the oil from the seeds and to manufacture the oil cake.

4. Process according to claim 3, also comprising, before step ii), at least one of the following steps i): crushing, hulling, preheating and/or drying of the seeds at a temperature of less than or equal to 100° C.

5. Process according to claim 1, also comprising a step iii) of flaking the oil cake before the reactive trituration step v).

6. Process according to claim 1, also comprising a step iv) of drying the oil cake at a temperature in the range from 60 to 140° C., before the reactive trituration step v).

7. Process according to claim 3, in which less than 72 hours pass between step ii) of manufacture of the oil cake and the reactive trituration step v).

8. Process according to claim 3, in which the steps are performed continuously.

9. Process according to claim 1, in which the oil cake has an acidity level of less than 10 mg KOH/g.

10. Process according to claim 1, in which the light alcohol is methanol.

11. Process according to claim 1, in which the alkaline catalyst is sodium hydroxide.

12. Process according to claim 1, in which the catalyst/alcohol/oil cake mass ratio is in the range 0.001 to 0.01/0.1 to 10/1.

13. Process according to claim 2, in which the light alcohol/cosolvent ratio is in the range from 10/90 to 90/10.

14. Process according to claim 1, in which the mixture comprising fatty acid esters and glycerol is subjected to a decantation step to obtain an upper phase predominantly composed of fatty acid esters and a lower phase predominantly composed of glycerol and water.

15. Process according to claim 14, in which the said upper phase is subjected to a succession of chemical reactions and/or of separations/purifications leading to the production of biodiesel.

16. Process according to claim 1, in which the oil cake is obtained from the pressing of castor oil seeds and the said fatty acid esters comprise ricinoleic acid ester.

17. Detoxified de-oiled cake obtained via the process of claim 1, having a content of phorbol esters of less than or equal to 0.3 mg/g.

* * * * *